United States Patent [19]

Michaud

[11] 4,270,539
[45] Jun. 2, 1981

[54] URINE COLLECTION APPARATUS

[76] Inventor: Robert A. Frosch, Administrator of the National Aeronautics and Space Administration, with respect to an invention of Roger B. Michaud, League City, Tex.

[21] Appl. No.: 34,531

[22] Filed: Apr. 27, 1979

[51] Int. Cl.³ .............................................. A61F 5/44
[52] U.S. Cl. ..................................... 128/295; 4/144.3
[58] Field of Search ................... 4/144.1, 144.2, 144.3; 128/294, 295, 283, 284

[56] References Cited

U.S. PATENT DOCUMENTS

| | | | |
|---|---|---|---|
| 2,382,276 | 8/1945 | Wells | 128/295 |
| 2,484,356 | 10/1949 | Ribeiro et al. | 128/295 |
| 3,864,759 | 2/1975 | Horiuchi | 4/144.3 |
| 4,023,571 | 5/1977 | Comerford et al. | 128/284 |
| 4,194,508 | 3/1980 | Anderson | 128/295 |

FOREIGN PATENT DOCUMENTS 1004104 1/1977 Canada ...................................... 128/295

*Primary Examiner*—Robert W. Michell
*Assistant Examiner*—J. L. Kruter
*Attorney, Agent, or Firm*—Edward K. Fein; John R. Manning; Marvin F. Matthews

[57] ABSTRACT

A urine collection device for females comprising an interface body having an interface surface for engagement with the user's body. The interface body comprises a forward portion defining a urine-receiving bore having an inlet in the interface surface adapted to be disposed in surrounding relation to the urethral opening of the user. The interface body further comprises a rear portion integrally adjoining the forward portion and having a non-invasive vaginal seal on the interface surface for sealing the vagina of the user from communication with the urine-receiving bore. An absorbent pad is removably supported on the interface body and extends laterally therefrom. Also disclosed is a garment for supporting the urine collection device.

34 Claims, 4 Drawing Figures

URINE COLLECTION APPARATUS

ORIGIN OF THE INVENTION

The invention described herein was made in the performance of work under a NASA contract and is subject to the provisions of Section 305 of the National Aeronautics and Space Act of 1958, Public Law 85-568 (Stat. 453; 45 U.S.C. 2457).

BACKGROUND OF THE INVENTION

1. Field of the Invention

The present invention pertains to urine collection devices, and more particularly, for such devices for use by females. Such apparatus is required, not only for those who are incontinent, but also for those who—for various reasons—are precluded from using ordinary restroom facilities for extended periods of time. For example, those who are bedridden and/or incapacitated but not incontinent, may have such needs. However, an even more challenging problem arises in the cases of active individuals who require a device which will not unduly interfere with their assuming of various postures or performances of activities such as walking, climbing, stooping, bending, etc. For example, certain occupations require that a person continuously wear specialized protective clothing, such as an astronaut spacesuit, for extended periods of time, and the fact that these garments may not be removed during those periods precludes the use of ordinary facilities. Likewise, those who must remain on duty at a work site much as a surgical theater for long periods of time may also require such devices.

Numerous problems have been encountered in the attempt to devise a suitable urine collection system for females. Not only must the system collect urine completely, i.e. without leakage, but it must also be comfortable and non-irritating to the user. The device must minimize contact of the urine with the user's body, both in terms of contact time and surface area involved. More particularly, it is necessary to prevent urine from entering the vagina or remaining in contact with the vaginal opening for, since urine provides a good growth medium for bacteria, such contamination can lead to serious vaginal infections. Finally, the device should be as inobtrusive and uninhibiting as possible and relatively free from aesthetically displeasing attributes such as unpleasant odors.

2. Description of the Prior Art

Probably the least acceptable of prior attempts to deal with urine collection in females is the use of a simple diaper or other absorbent garment or pad. These are obviously too uncomfortable, bulky, and aesthetically distasteful to be appropriate for an active individual who is either incontinent or occupationally prevented from using ordinary restrooms at times. Futhermore, even for an invalid, such garments are unacceptable because they generally retain a wet surface in contact with a relatively large area of the body, they do not prevent urine from contacting or entering the vagina, and in short, achieve virtually none of the objectives set forth above.

Internal catherization, another relatively primitive technique, is irritating, uncomfortable, and interferes with normal movements and activities. Thus, it is not acceptable for long term or repeated use, or even for short term use by active persons. The use of bedpans by persons who are bedridden but not incontinent is inconvenient, uncomfortable and messy, and requires the assistance of another person. Surgical implantation of valves, pacemakers or the like is expensive and risky.

The other major approach to the problem is that of providing a device which forms a receptacle held against the user's body so that it may collect urine which is emitted. The prior art devices falling within this category have been generally unacceptable for many reasons. Not only do most such devices fail to adequately seal the vaginal area from contact with urine, but they are also uncomfortable, unduly bulky, and/or limiting in terms of the activities in which the user may engage while wearing them. Additionally, many of the prior art devices in the latter class include invasive vaginal locators or positioning members. Not only are such members uncomfortable, but they may also interfere with normal menstrual hygiene and, in some cases, may actually tend to direct urine from the receptacle portion of the device into the vagina, rather than sealing it therefrom. Furthermore, prior receptacle type devices have typically been difficult to care for, and in particular, to keep clean and sanitary.

SUMMARY OF THE INVENTION

The present invention provides a urine collection device for females which may be completely, or at least substantially non-invasive, and which is designed for maximum comfort and minimum interference with ordinary activities on the part of the user. Furthermore, the device is highly effective in presenting leakage of urine therefrom, but is nevertheless provided with back-up features which prevent any small quantities which may leak from entering the vagina of the user, spilling, or otherwise causing problems. Furthermore, the device is easy to use and care for and adaptable for use in several different ways.

In particular, the urine collection device includes an interface body having an interface surface for engagement with the user's body. The interface body includes a forward portion defining a urine-receiving bore having an inlet in the interface surface adapted to be disposed in surrounding relation to the urethral opening of the user. The interface body further comprises a rear portion, integrally adjoining the forward portion, and having a non-invasive vaginal seal on the interface surface for sealing the vagina of the user from communication with the urine-receiving bore. The non-invasive seal makes the device more comfortable, easy to use, and less likely to cause vaginal infection, and also permits an ordinary menstrual tampon to be used with the device.

The interface body is preferably custom molded to precisely fit the anatomy of the individual user. Futhermore, the body is preferably formed of a substance which is or becomes somewhat flexible and resilient when in contact with the temperature and pressure of the user's body. Major portions of the walls defining the urine-receiving bore are preferably relatively thin and terminate in a sealing rim on the interface surface about at least a major portion of the inlet. This rim and the thin chamber walls continuous therewith, in conjunction with the aforementioned flexibility of the material in use, provides a highly effective seal about the urethral opening and minimizes the leakage of urine from the inlet. However, any urine which does leak is prevented from entering the vagina by the vaginal seal, which is preferably in the form of a lip-like seal ring extending from the interface surface. A non-invasive positioning member may be provided within the seal ring to engage the vaginal opening of the user so as to help keep the interface body, and more specifically the vaginal seal, properly located.

To collect and contain any urine which does leak from the device, an absorbent pad may be removably supported on the interface body and extending laterally therefrom below the interface surface. Preferably, the portion of the interface body located above the pad is sized to be received between the labia, and the pad itself is spaced from the interface surface by a distance such that it will underlie and abut the urogenital area. The pad itself may be of an improved form comprising a central body of wicking material surrounded by a casing of one-way permeable material, the upper and lower layers of which are secured together adjacent the outer edges of the pad. The pad also includes an expansible central opening to permit the pad to be emplaced on and removed from the interface body.

To support the pad, the interface body is preferably provided with a flange surrounding the interface body and extending laterally outwardly therefrom. The flange is located slightly below the intended position of the pad, and preferably at the lowermost extremity of the interface body.

The flange may also serve to removably support on the interface body a drain conduit. This conduit may have an inlet opening and an inwardly extending rim surrounding the inlet opening. Thus, the rim can be placed in overlying relation to the flange, below the pad, to connect the conduit to the interface body. The separability of the conduit and the interface body make the device easier to care for and store. This feature also permits one of these two parts to be replaced independently of the other. For example, the interface body, which is preferably customized, may be relatively expensive and thus designed for repeated use over a long period of time, while the drain conduit, which can be massed produced, may be made of a less expensive material so that it can be changed more frequently.

Finally, the invention further contemplates a specialized panty-like garment for supporting and positioning the urine collection device in use. The garment comprises a panty at least partially comprised of an absorbent natural fiber, such as cotton. Support means, such as a network of elasticized straps, are affixed to the panty and adapted to exert an upward force on the crotch portion of the panty so as to keep the urine collection device in sealing contact with the user's body. An opening may be provided in the crotch portion of the panty for accommodation of the drain conduit.

Accordingly, it is a principal object of the present invention to provide an improved urine collection device for females.

A further object of the present invention is to provide such a device having an effective, non-invasive vaginal seal.

Another object of the present invention is to provide a urine collection device which is small, comfortable, uninhibiting, and easy to care for.

Yet a further object of the present invention is to provide such a device having improved means for removably attaching a drain conduit to an interface body.

Yet another object of the present invention is to provide such a device having an improved absorbent pad removably mounted thereon.

Still another object of the present invention is to provide an improved garment for supporting such a device.

Still other objects, features, and advantages of the present invention will be made apparent by the following detailed description together with the accompanying drawings and the appended claims.

DESCRIPTION OF THE PREFERRED EMBODIMENTS

Figure 1:
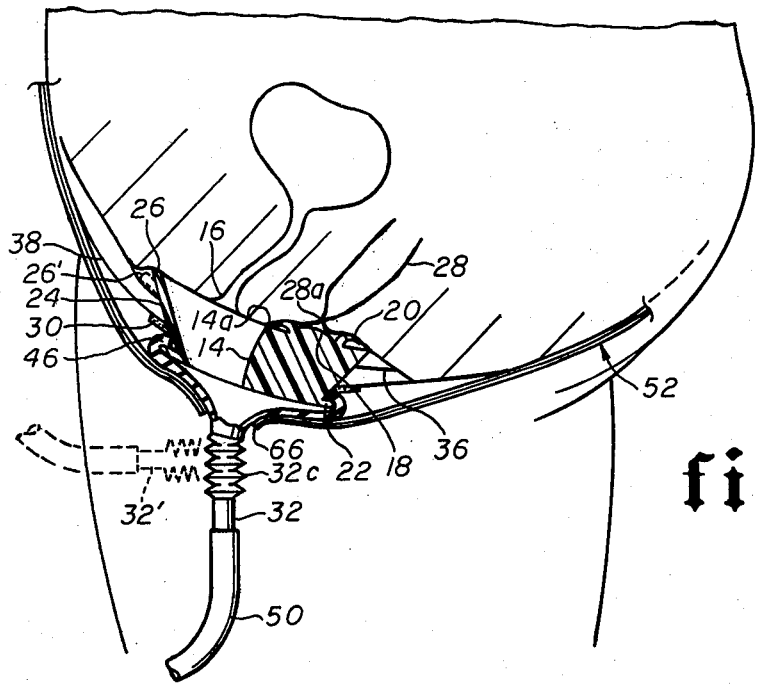
FIG. 1 is a ventral-dorsal cross-sectional view through a human body and a urine collection device according to the invention.
Figure 2:
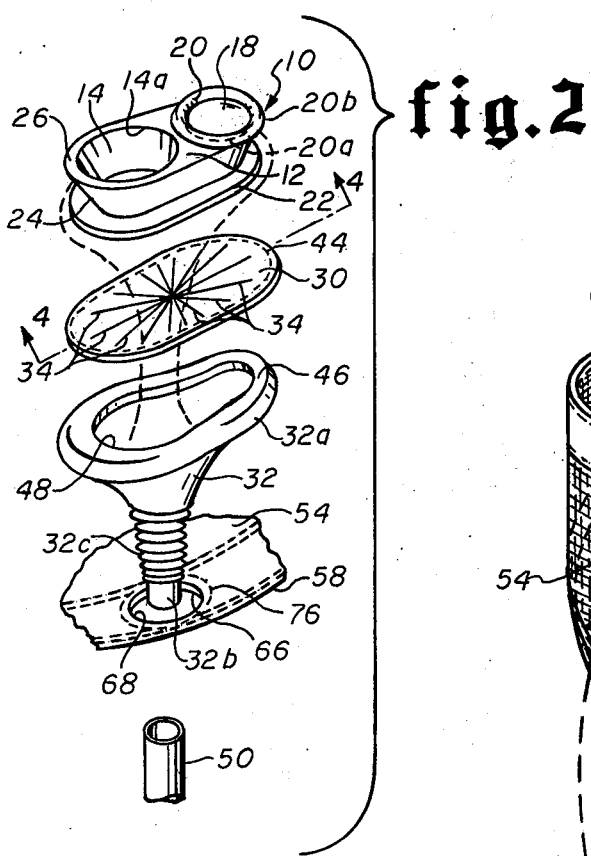
FIG. 2 is an exploded perspective view of the device of FIG. 1.

Referring first to FIGS. 1 and 2, there is shown a urine collection device and supporting garment as they might be assembled and used by one who is occupationally prevented from using ordinary restroom facilities for extended periods of time, for example, by an astronaut who must continuously wear special protective clothing and/or gear while outside the space vehicle. However, the device can be modified for other types of uses, as will be explained more fully below. The device includes an interface body 10 which is preferably integrally molded from a suitable synthetic material such as is described more fully below. As used herein, terms such as "upper," "lower," "forward," and "rear" will be used for convenience to describe the device at it appears in FIG. 1, i.e. when properly implaced on the body of a user and with the user in a standing position. However, it should be understood that the device could change orientation, as when the user moves about and when the device is removed from the user's body, and therefore such terms should not be construed in a limiting sense.

The interface body 10 has an uppermost interface surface 12 which is designed for engagement with the user's body. Interface body 10 may also be considered to be generally divided into forward and rear portions. The forward portion defines a urine-receiving bore 14 having an inlet 14a in the interface surface 12. Inlet 14a is sized and positioned to be disposed in surrounding relation to the urethral opening 16 of the user. The rear portion of interface body 10 includes a non-invasive vaginal positioning member 18 on interface surface 12 surrounded by a lip-like vaginal seal ring 20, also on interface surface 12. A flange 22, integrally molded with interface body 10, surrounds and extends laterally outwardly from the lowermost extremity of interface body 10.

To enhance the comfort as well as the sealing effectiveness of interface body 10, the upper portion thereof is preferably customized to fit the individual user by a medical molding technique. To further enhance these characteristics, the interface body 10 is preferably formed of a material or combination of materials which is resilient and flexible at human body temperature and pressure. In other words, the material is such that, when in contact with the temperature and pressure of the body in use, it will soften somewhat and tend to conform even more perfectly with the configuration of the anatomy of the individual user. Also, the material will have sufficient resiliency to properly seal against the user's body. Examples of preferred materials which have these characteristics and which are also medically acceptable for contact with the urogenital area are n-Propyl, n-Butyl and ethyl polymethacrylates. The flexibility and resiliency of the material in use also permits the interface body to accommodate the user's movements while still retaining a high degree of comfort and an effective seal.

More specifically, the forward portion of interface body 10 includes a relatively thin sectioned portion 24 defining the forward and side chamber walls of bore 14. Chamber walls 24 terminate in a thin generally u-shaped rim 26 on interface surface 12 defining the forward and side portions of inlet 14a. The thinness of walls 24 and rim 26 cooperates with the aforementioned characteristics of the material of which they are formed to permit rim 26 to form a comfortable but effective seal about the major portion of the urethral opening 16. Furthermore, these characteristics enable rim 26 to flex to accommodate various movements and postures of the user while still maintaining such a seal. For example, the position to which rim 26 would flex if the user were to assume a sitting position is shown in phantom at 26' in FIG. 1. The downwardly and inwardly tapered configuration of bore 14 and the surrounding chamber walls 24 also enhances this flexing ability. Accordingly, the device allows minimum leakage of urine from around the inlet 14a.

Any urine which should leak from inlet 14a is effectively prevented from entering the vagina 28 by seal 20. As shown in FIG. 2, seal 20, in its relaxed position, is curved or flared downwardly and outwardly from a base edge 20a integrally adjoined to interface surface 12 to a free edge 20b extending away from interface surface 12. As best shown in FIG. 1, the longitudinal cross section of seal 20 is gradually reduced from its base edge 20a to its free edge 20b. This configuration, coupled with the characteristics of the material from which seal 20 is formed, permit the free edge 20b to flex in use to form a fluid tight seal about the vaginal opening 28a as shown in FIG. 1. As mentioned, this seal is non-invasive, i.e. it does not enter the vagina 28. The positioning member 18 is slightly convex so that it may engage the natural indentation adjacent the vaginal opening or mouth 28a of the vagina 28. This forms a reference point to assist in proper positioning of the interface body 10, and more specifically of seal 20, with respect to the user's body. Nevertheless, the positioning member 18, like seal 20, is non-invasive, i.e. does not enter the vagina proper 28.

However, in cases where the user has difficulty positioning the device and/or maintaining it properly in place, member 18 may be modified by lengthening to form a vaginally invasive positioning pessary. Preferably such a pessary is only as long as is necessary to properly position the device, and more particularly is short enough so that it does not interfere with the use of a menstrual tampon. Similarly, while seal 20 is preferably non-invasive as shown, for certain individuals in whom the urethral opening is located within the vagina, an invasive positioning pessary with a surrounding invasive seal may be used. The seal would be positioned as needed for the individual to prevent urine from flowing even more deeply into the vagina.

The flange 22 serves primarily as a means for removably mounting two other portions of the device, a pad 30 and a drain conduit 32, on interface body 10. Pad 30 is disposed in laterally surrounding relation to the interface body to collect and contain any urine which might leak from the interface body, and likewise, to provide a soft, absorbent layer of material preventing direct contact of the user's body with the upper portion of the elastomeric drain conduit 32. More specifically, pad 30 is provided with an expansible central opening formed by radiating slits 34 whereby the pad may be slipped up and over the flange 22 to be supported thereby.

The portion of interface body 10 located generally above flange 22 is sized to be received between the labia minor 36 of the user. As previously mentioned, this upper portion of the interface body is preferably customized to fit the individual. However, flange 22 may be standardized for mass production. Flange 22 is spaced below the interface surface 12 by a distance such that, when pad 30 is implaced over flange 22, the pad will underlie and abut the labia major 38. Pad 30 is further sized and configured to underlie the major portion of the urogenital area without folding or crumpling. The pad 30 may be customized for the individual to more effecitvely achieve this result. This will normally require that it have a relatively wide rear end and a relatively narrow forward end, e.g. it may be somewhat teardrop shaped or ovoid as shown in FIG. 2.

Figure 4:
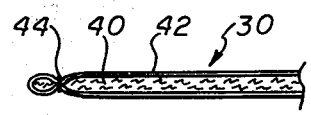
FIG. 4 is an enlarged partial sectional view through the improved pad of the invention.

As best seen in FIG. 4, the pad 30 is comprised of a central body 40 of any suitable wicking material including fibers, powders, gells, etc. Central body 40 is surrounded by a casing 42 of one-way permeable material. Thus, the urine will be drawn into body 40 and retained there, while casing 42 will prevent egress of urine from body 40 while also providing a dry surface for contact with the user's body. To prevent ballooning of the casing 42 about the laterally outer edges as body 40 becomes filled with liquid, the upper and lower edges of casing 42 are secured together adjacent the outer edges of the pad by stitches 44 which extend through both layers of the casing as well as the enclosed body 40. It should be understood that other means for securing the upper and lower casing layers, such as heat sealing techniques, could also be employed.

As previously mentioned, flange 22 serves not only to support the pad 30 but also to connect the drain conduit 32 to the interface body. Accordingly, conduit 32 has a relatively wide upper end including a laterally inwardly extending rim 46 defining an inlet opening 48. The configuration of the upper end of conduit 32 generally matches that of flange 22, and the conduit is formed of an elastomeric material so that rim 46 may be employed over flange 22 beneath pad 30 whereby flange 22 supports and retains the drainage conduit 32 via rim 46. As shown in FIG. 1, urine-receiving bore 14 extends all the way through interface body 10 and has a lower outlet opening into the upper end of the drainage conduit 32 when the latter is properly affixed to the interface body. Just below the portion of conduit 32 which is adapted to receive flange 22, its diameter is reduced to form a relatively small generally cylindrical main body portion 32b. Additional sections of tubing, such as that partially shown at 50, may be secured to portion 32b to extend the length of the drainage conduit as needed. Near the upper end 32a of the drainage conduit, and more specifically, adjacent its intersection with main body portion 32 the drainage conduit may be corrugated as indicated at 32c or otherwise convoluted to permit sharp bending thereof without collapse. For example, the position of the drainage conduit when the user is seated is shown in phantom at 32'. It will be understood that the downstream end of conduit extension 50 would be communicated with a suitable storage container, and that a pump could be provided to direct the urine into the container if needed.

As mentioned above, the upper portion of interface body 10 is sized to be comfortably received between the labia of the user. While the dimensions of both the urine collection device and the user's anatomy have been somewhat exagerated in FIG. 1 for purposes of illustration, the actual dimension of one such device custom molded for a test subject will illustrate the relatively small size of the device. This prototype was approximately 2 inches (5.08 cm.) long from the ventral to the dorsal extremeties of the interface surface 12. The depth of the device from the interface surface to the flange 22 was approximately ½ inch (1.27 cm.), and the thickness of the pad would range from ⅛ to 3/16 inches (0.318 to 0.476 cm.). It can also be seen that the reduction in width from the upper end 32a to the main body portion 32b of drainage conduit 32 is rather abrupt, i.e. occurs over a relatively short longitudinal extent of said conduit. Thus, the portions of the device immediately adjacent the urogenital area are extremely small, and the only portion of the device which extends substantially beyond the urogenital area is the relatively small diameter portion of drainage conduit 32 and its extension 50. This small size enhances the comfort and inobtrusiveness of the device in use. It is particularly noted that the small vertical dimension of the device (exclusive of the small diameter portion of conduit 32), together with the drain conduit convolutions 32c, allow the user to comfortably assume a sitting position. Nevertheless, for reasons mentioned above, the effectiveness of the device in completely collecting and properly containing the urine is extremely high.

Figure 3:
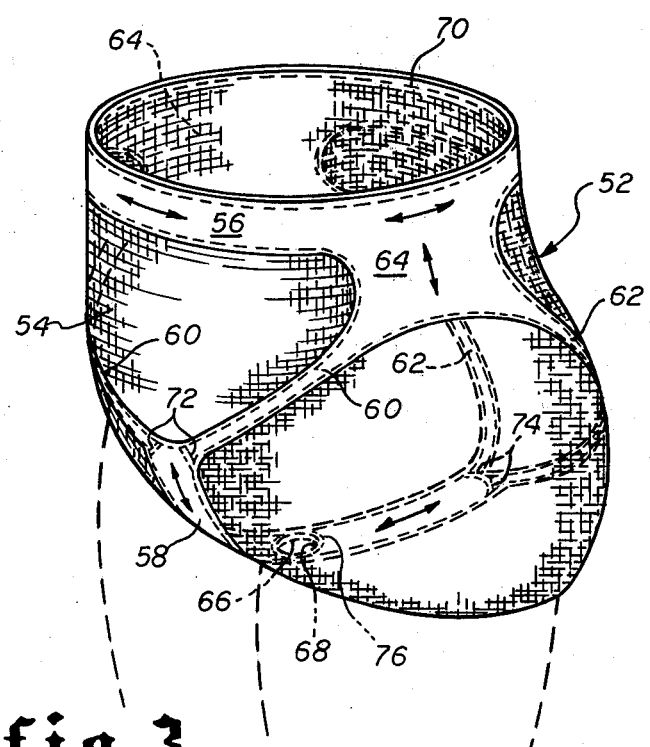
FIG. 3 is a perspective view of the supporting garment.

To assist in properly positioning the urine collection device and maintaining it in proper sealing engagement with the body, a specialized garment 52 has been devised. As shown in FIGS. 1 and 3, the garment 52 includes a panty 54 at least partially comprised of cotton or some other suitable absorbent natural fiber. Support means are affixed to the exterior of the panty 54 and adapted to exert an upward force on the crotch portion of the panty when in place on the user's body. Thus, when the garment is worn over the urine collection device, the latter is held in firm contact with the user's body.

Referring more specifically to FIG. 3, the support means include a waist band 56, preferably at least ½ in. (about 1.3 cm.) in width, and a crotch strap 58 with its longer dimension extending in the ventral dorsal direction along the crotch portion of the panty. A pair of ventral straps 60 diverge upwardly from the forward end of the crotch strap 58, and a pair of dorsal straps 62 similarly diverge upwardly from the rear end of crotch strap 58. A pair of side panels 64 depend downwardly from respective side portions of the waist band 56, and each side panel 64 is adjoined to a respective one of the ventral straps 60 and a respective one of the dorsal straps 62. Preferably, the entire network consisting of waistband 56, panels 64, and straps 58, 60, and 62 is comprised of an elastic material such as that known commercially as "lycra spandex." In any event, at least the ventral strap 60, dorsal strap 62, and side panels 62 should be elastic whereby they may serve to pull the crotch strap 58 upwardly with respect to waist band 56. As is known in the art, lycra spandex and similar materials have greater elasticity in one of two perpendicular directions. As indicated by the arrows in FIG. 3, the material is preferably arranged so that the direction of greater elasticity is lengthwise within the waist band 56, crotch strap 58, ventral straps 60 and dorsal straps 62, and vertical in the side panels 64. Aligned openings 66 and 68 (see FIG. 2) are provided in the crotch strap 58 and crotch portion of panty 54 respectively to permit the drainage conduit 32 to extend therethrough.

The elastic portions of garment 52 are reinforced by stitching 70 along all edges thereof. Additional transverse reinforcing stitching 72 is provided at the intersections of ventral straps 60 and crotch strap 58. Similarly, transverse reinforcing stitching 74 is provided at the intersections of dorsal strap 62 and crotch strap 68, and reinforcing stitching 76 is provided about the periphery of openings 66 and 68.

The garment 52 is designed not only to provide proper support and positioning of the urine collection device, but also for maximum comfort to the user. As shown, the cotton panty 54 has the elastic member stitched to the exterior thereof. Alternatively the elastic portions may be interwoven with the panty. In any case, there should be an inner layer of soft absorbent material adjacent the skin to prevent irritating contact between the skin and the elastic members. Furthermore, even though the elastic network provides a fairly strong upward force on the crotch portion of the panty, the diverging arrangement of the ventral straps 60 avoids uncomfortable pressure on the abdomen. Further to this end, it is desirable that the forward end portion of crotch strap 58 not extend upwardly beyond the pubic bone, and the side panels 64 preferably overlie the hip bones in use. Thus, the force of the elastic members is taken by the user's bone structure rather than by the abdomen, of soft organs or tissues. To enhance the ease of donning and doffing the garment, it may be provided with openings along one or both sides with zippers, hooks and eyes, or other suitable closure means.

As mentioned above the foregoing represents a typical embodiment of the invention primarily intended for active individuals who are precluded from using ordinary restrooms for prolonged periods of time. However, it will be appreciated that numerous modifications could be made to adapt the device for other uses. For example, the interface body 10 and drainage conduit 32 could be used without the pad 30 and garment 52 but in conjunction with a suitable container located at the downstream end of tube 50 as a portable hand-held urinal, e.g. for persons who are bedridden but not incontinent. When used in this manner, flange 52 provides a convenient member for holding the device by hand.

Another modification might involve adaptation of the device for use by incontinent persons of the type who pass small quantities of urine almost continuously, rather than a relatively large volume at once. For this use, the urine receiving bore 14 might be filled, or at least partially lined, with a suitable wicking material, preferably a one-way wicking material arranged to direct the urine away from the user's body. For such persons, the device itself, and particularly the urine-receiving bore, might be enlarged, the bottom of the bore closed by a lower wall, and the drainage tube completely eliminated. The improved pad, including the one-way permeable casing with the upper and lower layers thereof secured together adjacent the edges may be adapted for separate use as a menstrual pad. Likewise, the garment of FIG. 3 might be used to support a menstrual pad, a urine-collection device other than that of the present invention, other medical of hygiene devices, and/or the urogenital organs themselves.

Numerous other modifications will suggest themselves to those of skill in the art. Accordingly, it is intended that the scope of the present invention be limited only by the claims which follow.

What is claimed is:

1. A urine collection device for human females comprising:
   an interface body having an interface surface for engagement with the user's body, said interface body comprising a forward portion defining a urine-receiving bore having an inlet in said interface surface adapted to be disposed in surrounding relation to the urethral opening of the user, said interface body further comprising a rear portion integrally adjoining said forward portion and having a vaginal seal including an elevated lip portion on said interface surface for sealing the vagina of the user from communication with said urine-receiving bore;
   and an absorbent pad removably supported on said interface body and extending laterally therefrom.

2. The device of claim 1 wherein said vaginal seal is substantially non-invasive and is adpated to seal about the periphery of the vaginal opening of the user.

3. The device of claim 2 wherein said vaginal seal is a lip-like seal ring having a base edge adjoining said interface surface and a free edge extending away from said interface surface.

4. The device of claim 3 wherein said seal ring is flared outwardly from its base edge to its free edge and is comprised of a material which is relatively rigid at normal room temperatures, but becomes more flexible and resilient at human body temperature such as to readily conform to the configuration of the user's anatomy when subjected to the pressure of the user's body against the material.

5. The device of claim 3 wherein said interface body further comprises a positioning member within said seal ring and adapted to engage the vaginal opening of the user.

6. The device of claim 5 wherein said positioning member is substantially non-invasive.

7. The device of claim 1 wherein said forward portion of said interface body forms a sealing rim about at least a major portion of said inlet for sealing about the urethral opening of the user.

8. The device of claim 7 wherein said forward portion of said interface body includes relatively thin chamber wall means continuous with said rim and defining a major portion of said urine-receiving bore.

9. The device of claim 8 wherein said rim and said chamber wall means are comprised of a material which is relatively rigid at normal room temperatures, but becomes more flexible and resilient at human body temperatures such as to readily conform to the configuration of the user's anatomy when subjected to the pressure of the user's body against the material.

10. The device of claim 7 wherein said interface body is comprised of a material which is relatively rigid at normal room temperatures, but becomes more flexible and resilient at human body temperature such as to readily conform to the configuration of the user's anatomy when subjected to the pressure of the user's body against the material.

11. The device of claim 1 further comprising support means extending laterally from said interface body to underlie and support said pad.

12. The device of claim 11 wherein said support means comprises a flange laterally surrounding said interface body distal said interface surface.

13. The device of claim 12 further comprising a drain conduit having an inlet opening and an inwardly extending rim surrounding said inlet opening and overlying said flange to removably support said drain conduit on said interface body, and said urine-receiving bore of said interface body further having an outlet communicating with the inlet opening of said drain conduit.

14. The device of claim 13 wherein said drain conduit is flexible and resilient.

15. The device of claim 14 wherein said drain conduit has a relatively wide upper end for receipt of said flange and a relatively narrow main body.

16. The device of claim 15 wherein said main body includes a convoluted section near said interface body to permit bending of said drain conduit without collapse thereof.

17. The device of claim 1 wherein said urine-receiving bore further includes an outlet opening generally away from said inlet, the device further comprising a flexible drain conduit removably attached to said interface body in communication with said outlet.

18. The device of claim 1 wherein said pad comprises a central body of wicking material surrounded by a casing of one-way permeable material.

19. The device of claim 18 wherein said pad comprises a relatively wide rear end and a relatively narrow forward end.

20. The device of claim 18 wherein the upper and lower layers of said casing are secured together adjacent the edges of said pad.

21. The device of claim 18 wherein said pad laterally surounds said interface body.

22. The device of claim 21 wherein said pad has an expansible central opening for permitting said pad to be placed in surrounding relation to said interface body.

23. A urine collection device for human females comprising:
   an interface body having an interface surface for engagement with the user's body, said interface body comprising a forward portion defininig a urine-receiving bore having an inlet in said interface surface adapted to be disposed in surrounding relation to the urethral opening of the user, said interface body further comprising a rear portion integrally adjoining said forward portion and having a non-invasive vaginal seal including an elevated lip portion on said interface surface for sealing the vagina of the user from communication with said urine-receiving bore.

24. The device of claim 23 further comprising flange means extending laterally outwardly from said interface body distal said interface surface.

25. The device of claim 24 wherein said flange means laterally surounds said interface body.

26. The device of claim 25 further comprising a drain conduit having an inlet opening and an inwardly extending rim surrounding said inlet opening and overlying said flange to removably support said drain conduit on said interface body, said urine-receiving bore of said interface body further having an outlet communicating with the inlet opening of said drain conduit.

27. The device of claim 26 wherein said drain conduit has a relatively wide upper end for receipt of said flange and a relatively narrow main body.

28. The device of claim 23 wherein said vaginal seal is a lip-like seal ring having a base edge adjoining said interface surface and a free edge extending away from said interface surface.

29. The device of claim 28 wherein said seal ring is comprised of a material which is flexible and resilient at human body temperature and pressure.

30. The device of claim 28 wherein said interface body further comprises a positioning member within said seal ring and adapted to engage the vaginal opening of the user.

31. The device of claim 30 wherein said positioning member is substantially non-invasive.

32. The device of claim 23 wherein said forward portion of said interface body forms a sealing rim about at least a major portion of said inlet for sealing about the urethral opening of the user.

33. The device of claim 32 wherein said forward portion of said interface body includes relatively thin chamber wall means continuous with said rim and defining a major portion of said urine-receiving bore.

34. The device of claim 33 wherein said rim and said chamber wall means are comprised of a material which is relatively rigid at normal room temperatures but becomes more flexible and resilient at human body temperatures such as to readily conform to the configuration of the user's anatomy when subjected to the pressure of the user's body against the material.

* * * * *